(12) United States Patent
Sunden et al.

(10) Patent No.: US 11,426,079 B1
(45) Date of Patent: Aug. 30, 2022

(54) METHODS, SYSTEMS, AND DEVICES FOR IMPROVED SKIN TEMPERATURE MONITORING

(71) Applicant: Fitbit, Inc., San Francisco, CA (US)

(72) Inventors: Lindsey Sunden, San Francisco, CA (US); Aniket Deshpande, Mountain View, CA (US); Belen Lafon, Mountain View, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 17/380,804

(22) Filed: Jul. 20, 2021

(51) Int. Cl.
*A61B 5/01* (2006.01)
*A61B 5/00* (2006.01)
*G01K 13/20* (2021.01)
*G16H 50/20* (2018.01)

(52) U.S. Cl.
CPC .............. *A61B 5/01* (2013.01); *A61B 5/681* (2013.01); *A61B 5/7264* (2013.01); *G01K 13/20* (2021.01); *G16H 50/20* (2018.01); *A61B 2560/0252* (2013.01); *A61B 2562/0271* (2013.01)

(58) Field of Classification Search
None
See application file for complete search history.

(56) References Cited

U.S. PATENT DOCUMENTS

| | | | |
|---|---|---|---|
| 10,809,132 | B2 | 10/2020 | Buydens |
| 10,942,067 | B2 | 3/2021 | Pan |
| 2014/0163765 | A1 | 6/2014 | Jain et al. |
| 2015/0057963 | A1* | 2/2015 | Zakharov ............... A61B 5/01 702/131 |
| 2015/0297146 | A1 | 10/2015 | Pollack et al. |
| 2016/0018273 | A1* | 1/2016 | Jordan ................. G01K 7/015 702/130 |
| 2018/0092545 | A1* | 4/2018 | Kim .................... A61B 5/6824 |
| 2018/0184902 | A1* | 7/2018 | Meyerson ............ A61B 5/0008 |
| 2018/0184908 | A1* | 7/2018 | Meyerson ............. G01K 7/427 |
| 2018/0242850 | A1* | 8/2018 | Ellis ....................... G16H 40/67 |
| 2018/0245986 | A1* | 8/2018 | Pan ........................ G01K 1/20 |

(Continued)

FOREIGN PATENT DOCUMENTS

| CN | 112763099 | 5/2021 |
|---|---|---|
| WO | WO 2021/076642 | 4/2021 |

OTHER PUBLICATIONS

Song et al., "Wearable Continuous Body Temperature Measurement Using Multiple Artificial Neural Networks", IEEE Transactions on Industrial Informatics, vol. 14, No. 10, 2018, pp. 4395-4406.

(Continued)

*Primary Examiner* — Benjamin S Melhus
(74) *Attorney, Agent, or Firm* — Dority & Manning, P.A.

(57) ABSTRACT

The present disclosure provides computer-implemented methods, systems, and devices for improved skin temperature monitoring. Accurate estimates of skin and ambient temperature are generated based on determinations and comparisons of skin and internal device temperature sensor measurements contained on or within example devices. The estimates of skin and ambient temperature measurements facilitate monitoring skin and core temperature changes, detecting physiological events of a wearer of example devices, and determining when skin temperature changes are environmentally or physiologically induced.

13 Claims, 10 Drawing Sheets

(56) References Cited

U.S. PATENT DOCUMENTS

| | | | |
|---|---|---|---|
| 2019/0021701 A1* | 1/2019 | Vardi | A61B 5/4857 |
| 2019/0285488 A1* | 9/2019 | Lundstrom | G01K 13/20 |
| 2019/0323895 A1* | 10/2019 | Kostopoulos | G01J 5/0025 |
| 2020/0000441 A1* | 1/2020 | Lafon | A61B 5/742 |
| 2020/0217727 A1* | 7/2020 | Heitz | G01K 7/22 |
| 2020/0297328 A1* | 9/2020 | Webster | A61B 5/6847 |

OTHER PUBLICATIONS

International Search Report and Written Opinion for Application No. PCT/US2021/051643, dated Apr. 11, 2022, 17 pages.

\* cited by examiner

METHODS, SYSTEMS, AND DEVICES FOR IMPROVED SKIN TEMPERATURE MONITORING

FIELD

The present disclosure relates generally to health monitoring and wearable devices for health monitoring. More particularly, the present disclosure relates to methods and devices for improved skin temperature monitoring.

BACKGROUND

Skin temperature data can be dominated by shifts in ambient temperature. Devices that provide for skin temperature monitoring can thus introduce inaccuracies that are unrelated to sensor error. Methods, systems, and devices are needed to distinguish skin temperature changes that are physiologically induced from skin temperature changes that are environmentally induced.

SUMMARY

Aspects and advantages of embodiments of the present disclosure will be set forth in part in the following description, or can be learned from the description, or can be learned through practice of the embodiments.

One example aspect of the present disclosure is directed to a computer-implemented method for providing improved skin temperature monitoring. The method comprises determining, by a computing system comprising one or more computing devices, an internal device temperature of a wearable device worn by a user based on sensor data received from an internal device temperature sensor contained within the wearable device. The method also comprises determining, by the computing system, a first estimate of a skin temperature of the user based on sensor data received from a skin temperature sensor contained on or within the wearable device. Next, the method involves estimating, by the computing system, an ambient air temperature based at least in part on the first estimate of the skin temperature and the internal device temperature. The method then comprises refining, by the computing system, the first estimate of the skin temperature based at least in part on the estimated ambient air temperature to generate a second estimate of the skin temperature.

Another example aspect of the present disclosure is directed to a wearable device, comprising a device housing configured to be worn by a user, one or more processors included within the device housing, one or more skin temperature sensors included on or within the device housing and configured to produce skin temperature sensor data, one or more internal device temperature sensors included within the device housing and configured to produce internal device temperature sensor data, non-transitory computer-readable memory included within the device housing and storing instructions that, when executed by the one or more processors, cause the wearable device to perform operations. In particular, the operations comprise determining an internal device temperature within the device housing based at least in part on the internal device temperature sensor data received from the one or more internal device temperature sensors contained within the wearable device; determining a first estimate of a skin temperature of the user based on sensor data received from a skin temperature sensor included on or within the device housing; estimating an ambient air temperature based at least in part on the first estimate of the skin temperature and the internal device temperature; and refining the first estimate of the skin temperature based at least in part on the estimated ambient air temperature to generate a second estimate of the skin temperature.

Another example aspect of the present disclosure is directed to a computer-implemented method for providing improved skin temperature monitoring. The method comprises determining, by a computing system comprising one or more computing devices, an internal device temperature of a wearable device worn by a user based on sensor data received from an internal device temperature sensor contained within the wearable device. Next, the method comprises determining, by the computing system, a first estimate of a skin temperature of the user based on sensor data received from a skin temperature included on or within the wearable device. The method next involves refining, by the computing system, the first estimate of the skin temperature based at least in part on the internal device temperature of the wearable device to generate a second estimate of the skin temperature. The method then comprises determining, by the computing system, one or more physiological events based at least in part on the second estimate of the skin temperature.

BRIEF DESCRIPTION OF THE DRAWINGS

Detailed discussion of embodiments directed to one of ordinary skill in the art is set forth in the specification, which makes reference to the appended figures, in which.

DETAILED DESCRIPTION

Overview

Figure 1:
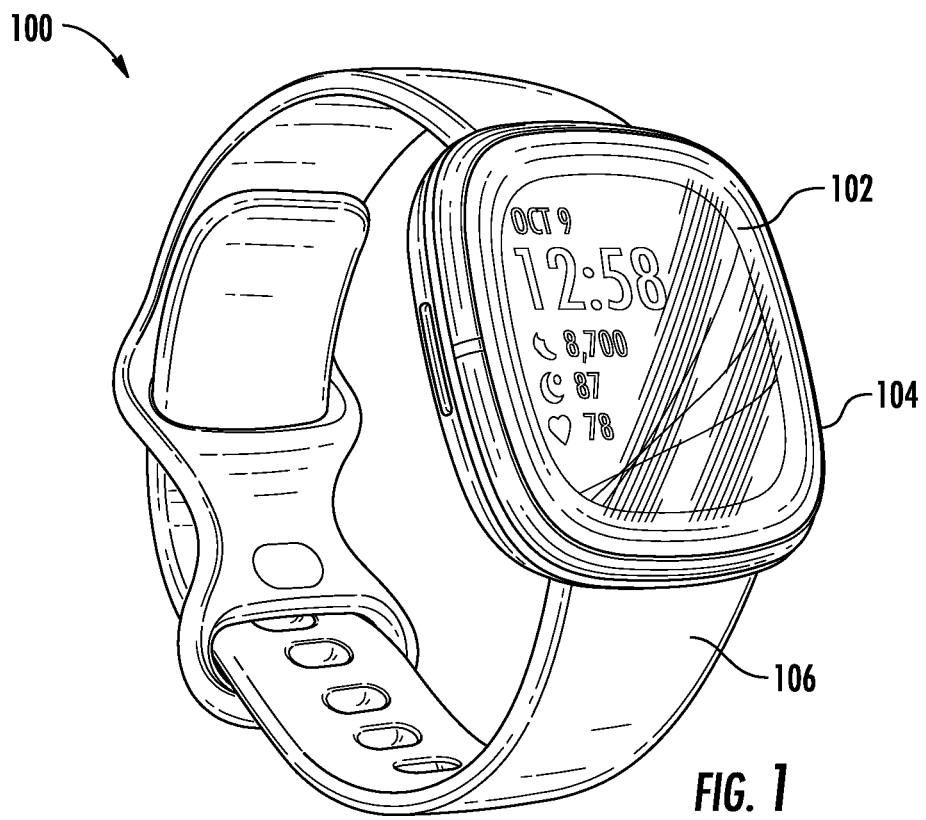
FIG. 1 depicts a front view of an example wearable device according to example embodiments of the present disclosure.

Generally, the present disclosure is directed to health monitoring and wearable devices for health monitoring, such as methods and devices for improved skin temperature monitoring. In particular, example aspects of the present disclosure involve computer-implemented methods for providing improved skin temperature monitoring. The methods of the present disclosure allow for the observation of meaningful changes in a person's core temperature and the identification of physiological trends and events relevant to a person's health.

More particularly, a person's skin temperature is expected to change with shifts in the person's core temperature. At times, there can be a positive correlation between a person's skin temperature and a person's core temperature, while at other times this relationship can result in inverse changes. For example, sometimes a person's body increases its core temperature to induce fever, and does so by reducing perfusion in the extremities, so a lower skin temperature is expected while the person's core temperature is increasing. These physiologically induced developments allow for the possibility of observing trends from a comparison of temperature data streams that may not be possible by observing other data streams. On the other hand, skin temperature changes can also be dominated by shifts in ambient temperature, making it difficult to identify skin temperature changes associated with physiological changes. Given this, methods are needed to distinguish skin temperature changes that are physiologically induced from changes that are environmentally induced.

In view of such challenges, the present disclosure provides computer-implemented systems and methods for improved skin temperature monitoring. In some implementations, the methods of the present disclosure involve a computing system determining an internal temperature of a wearable device worn by a user based at least in part on sensor data from one or more sensors contained within the wearable device. In an example, the wearable device may be a wristband, a bracelet, a wristwatch, an armband, a ring placed around a digit of the user, or other wearable products that may be equipped with sensors as described in the present disclosure. As another example, the one or more sensors that measure the internal temperature of the device may be contained within a housing of the wearable device, but may not be in thermal contact with the user's skin. When the one or more sensors that measure the internal temperature of the device are arranged according to this example, the sensors may be correlated with the user's skin temperature, but may also be more impacted by the temperature of outside air, for example, as compared to a dedicated skin temperature sensor.

According to another aspect, the methods of the present disclosure involve a computing system determining a first estimate of a skin temperature of a user based on sensor data received from one or more skin temperature sensors in thermal contact with the user and contained within the wearable device. In another example, the wearable device can include a thermally conductive baseplate configured to be in contact with the user's skin. In this example, the one or more skin temperature sensors can be configured to measure the temperature of the baseplate. When the one or more sensors that measure a first estimate of a user's skin temperature are arranged in this manner, the sensors may be less impacted by the temperature of the outside air, for example, as compared to the internal device temperature sensor described above and/or a dedicated ambient air temperature sensor.

According to another aspect of the present disclosure, the computing system can estimate an ambient air temperature based at least in part on the first estimate of the skin temperature and the internal device temperature. In some implementations, the computing system estimates the ambient air temperature by determining a difference between the first estimate of skin temperature and the internal temperature of the wearable device. In an example, the estimated ambient air temperature may be the product of one or more smoothing or curve fitting processes of data sets corresponding to temperature differentials as described above. In some implementations, the computing system may estimate the ambient air temperature by processing the first estimate of skin temperature and the internal temperature of the wearable device with a machine-learned model. As one example, the machine learned model can include a linear regression model, a neural network (e.g., recurrent neural network), or a clustering model. In some implementations, the computing system may receive the ambient air temperature as a prediction output by the machine-learned model.

According to another aspect of the present disclosure, the computing system can produce an intermediate estimate of skin temperature based at least in part on the first estimate of skin temperature and the internal device temperature. This intermediate estimate of skin temperature can be further refined based at least in part on the ambient temperature estimate to aid in generating a second estimate of skin temperature. In an example, the intermediate estimate of skin temperature may be the product of one or more smoothing or curve fitting processes of data sets corresponding to temperature differentials as described above. In some implementations, the computing system may generate the intermediate estimate of skin temperature by processing the first estimate of skin temperature and the internal temperature of the wearable device with a machine-learned model. As one example, the machine learned model can include a linear regression model, a neural network (e.g., recurrent neural network), or a clustering model. In some implementations, the computing system may receive the intermediate estimate of skin temperature as a prediction output by the machine-learned model.

In some implementations, the computing system can adjust the ambient air temperature estimate based at least in part on additional ambient sensor data taken from additional ambient sensors contained within the wearable device. In some implementations, the additional ambient sensors can include location sensors (e.g., global-positioning sensors), geo-sensors, weather sensors, motion sensors, altitude sensors, altimeter temperature sensors, ambient light sensors, heart rate sensors, and other physiological sensors. In an example, the computing system may observe whether an ambient light sensor contained within the wearable device is covered or not covered. In this example, the computing system may infer a warmer ambient temperature based on the ambient light sensor being covered, which can aid in the determination of skin temperature estimates and thus physiological trends based on skin temperature, skin temperature changes, and the rate of skin temperature changes. In some implementations, the computing system can adjust the ambient air temperature estimate based at least in part on sleep data of the user collected by the wearable device. In some implementations, examples of sleep data can include data to indicate whether the user is awake or asleep, a sleep coefficient of the user, and the heart rate of the user. If the user is asleep, the data can also include information to indicate whether the user is moving (e.g., repositioning) and a characterization of the type of sleep the user is experiencing (e.g., restless sleep, light sleep, deep sleep, rapid eye movement (REM) sleep). In an example, the computing system may infer that repositionings of a user during sleep are a function of the user's thermoregulatory cycle and thus aid in a determination of a user's core temperature based at least in part on the second estimate of the user's skin temperature.

According to another aspect of the present disclosure, the methods involve the computing system refining the first estimate of the skin temperature based at least in part on the estimated ambient air temperature or the intermediate estimate of skin temperature to generate a second estimate of the skin temperature. In an example, the second estimate of the skin temperature may be the product of one or more smoothing or curve fitting processes of data sets corresponding to the estimated ambient air temperature. In some implementations, the computing system modifies a confidence value associated with the second estimate of skin temperature or the estimated ambient air temperature. As one example, the confidence value can increase as the temperature differential between the first estimate of skin temperature or the estimated ambient air temperature and the internal temperature of the wearable device decreases. Stated differently, a smaller temperature differential between the first estimate of skin temperature or the estimated ambient air temperature and the internal temperature of the wearable device can equate to greater trust in the second estimate of skin temperature. As another example, a smaller temperature differential can also mean it is less likely ambient temperature is causing changes in the skin temperature of a user.

According to another aspect of the present disclosure, the methods involve the computing system determining one or more physiological events of a user based at least in part on the second estimate of skin temperature. In some implementations, the physiological events may include a fever, a circadian rhythm, a menstruation cycle, ovulation, heat stress, and thermal comfort. Detection of the physiological events can include detection or determination of a status of the physiological event such as detection of an onset of the physiological event, determination of an ongoing status of the event, and/or predictions about a future status of the event (e.g., peak fever expected to occur in next six hours). In an example, the computing system may detect a fever by smoothing a dataset of second estimates of skin temperature collected after an elevation in a user's skin temperature.

In some implementations, the computing system can estimate a core temperature of a user based on the second estimate of skin temperature. In an example, the estimated core temperature of the user may be based on second estimates of skin temperature collected at varying frequencies and during different sleep stages of the user (e.g., awake or asleep). In some implementations, the computing system distinguishes core temperature changes that are physiologically induced from core temperature changes that are environmentally induced. In some implementations, the computing system can monitor a rate of change in the second estimate of skin temperature to detect a transition in the second estimate of skin temperature. As one example, the computing system can determine physiological events based on the detected transition. In some examples, the physiological events may include an onset of fever, a circadian rhythm, a menstruation cycle, ovulation, heat stress, and thermal comfort.

The methods and devices of the present disclosure provide a number of technical effects and benefits including the determination of higher confidence estimates of a person's true skin temperature, observation of meaningful changes in a person's core temperature, and the identification of physiological trends and events relevant to a person's health.

The present disclosure also enables the refinement of data received from sensors within the wearable device by combining and analyzing data from multiple sensors in a way that allows the user to observe more than just raw data, but also trends and events inferred from the data. In this way, the present disclosure can also obviate the need for additional sensors within the wearable device, thereby saving device space and processor usage. The present disclosure also allows for more accurate devices to monitor skin temperature by implementing a device's sensors in ways that are more efficient, predictable, and useful.

With reference now to the Figures, example embodiments of the present disclosure will be discussed in further detail.

Example Methods, Systems, and Devices

FIG. 1 depicts a front view of an example wearable device 100 according to example embodiments of the present disclosure. Although the wearable device 100 of FIG. 1 is a wristwatch, the systems and methods of the present disclosure can be applied to any different type of wearable device such as, for example, a wristband, a bracelet, a wristwatch, an armband, a headband, eyeglasses, an earbud, a ring placed around a digit of a user, items of clothing having computers embedded therein, and/or other wearable products that may be equipped with sensors as described in the present disclosure. The wearable device 100 may be configured with a display 102, a device housing 104, and a band 106.

In some implementations, the wearable device 100 can be configured to communicate data to a user via the display 102 and/or any other data output devices such as haptic devices, light emitting diodes, etc. The data that is communicated can include data relating to skin temperature, heart rate, sleep state (e.g., light, deep, and REM sleep), sleep coefficient (e.g., sleep score), and other physiological data of the user (e.g., blood oxygen level). The display 102 can also be configured to communicate data from additional ambient sensors contained in or on the wearable device 100. Example information communicated by the display 102 from these additional ambient sensors can include a positioning, altitude, and weather of a location associated with the user. The display 102 can also communicate data regarding motion of the user (e.g., whether the user is stationary, walking, and/or running).

In some implementations, the display 102 can be configured to display information about physiological events of the user. Example physiological events that may be displayed include a fever, a circadian rhythm, a menstruation cycle, ovulation, heat stress, and thermal comfort of the user. The display 102 can also communicate information relating to detection of the physiological events of the user. Configured this way, the display 102 can communicate to the user a detection or determination of a status of the physiological event such as detection of an onset of the physiological event, determination of an ongoing status of the event, and/or predictions about a future status of the event (e.g., peak fever expected to occur in next six hours).

The display 102 or other data input device (e.g., various touch sensors and/or physical buttons, switches, or toggles) can also be configured to receive data input by the user. Examples of data input by the user can include information about symptoms, sleep conditions, ovulation, menstruation, and other physiological information related to the user's health.

The device housing 104 can be configured to contain one or more sensors. Example sensors contained by the device housing 104 can include skin temperature sensors, internal device temperature sensors, location sensors (e.g., GPS), motion sensors, altitude sensors, heart rate sensors, and other physiological sensors (e.g., blood oxygen level sensors). The device housing 104 can be configured to include one or more processors.

The band 106 can be configured to secure the wearable device 100 around an arm of the user by, for example, connecting ends of the band 106 with a buckle, clasp, or other similar securing device, thereby allowing the wearable device 100 to be worn by the user.

Figure 2:
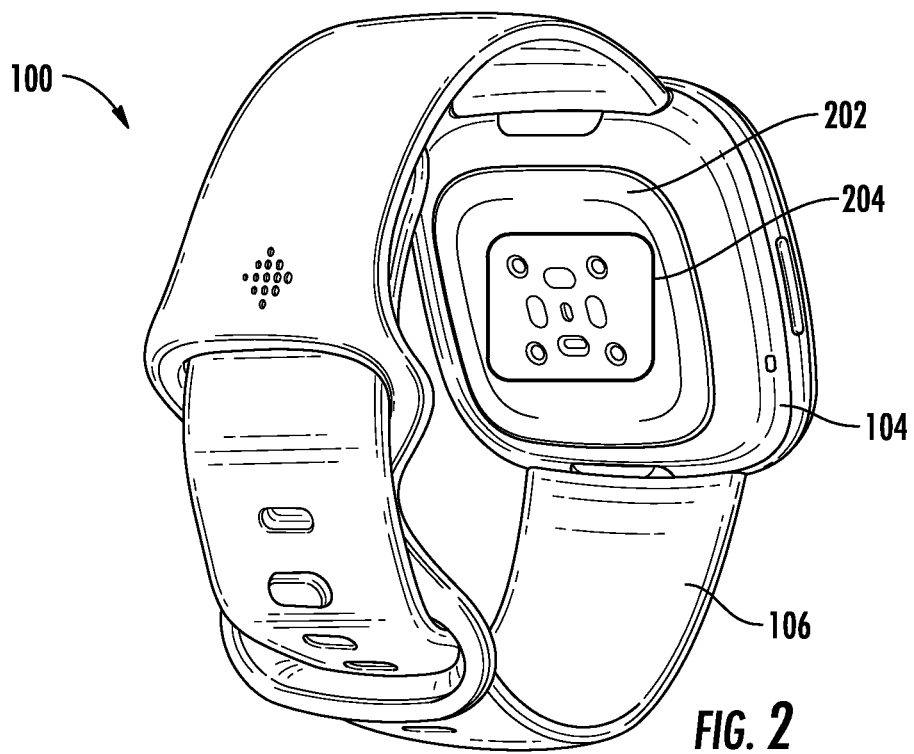
FIG. 2 depicts a rear view of an example wearable device according to example embodiments of the present disclosure.

FIG. 2 depicts a rear view of an example wearable device 100 according to example embodiments of the present disclosure. The wearable device 100 can be configured with a baseplate 202. The wearable device 100 can also be configured with one or more sensors 204 that can be affixed to the baseplate 202. Example sensors 204 can include skin temperature sensors, location sensors (e.g., GPS), motions sensors, altitude sensors, heart rate sensors, altimeter temperature sensors, and other physiological sensors (e.g., blood oxygen level sensors). The baseplate 202 can be thermally conductive and can be configured to be in thermal contact with the user and/or skin temperature sensors when the wearable device 100 is worn by the user. For example, when worn, the baseplate can press against the user's skin. Likewise, a skin temperature sensor can be configured to generate a temperature reading for the baseplate. In this way, the baseplate 202 can be configured to enable a skin temperature measurement of the user when the baseplate 202 is in thermal contact with the user (e.g., with the temperature of the baseplate serving as a proxy for the skin temperature of the user).

Although some example implementations use a baseplate for reading the temperature of a user's skin, other approaches can be used as well, including a temperature sensor configured to be in direct contact with the user's skin. In another example, an infrared sensor can be included in the device 100 (e.g., within the housing 104) and can measure the temperature of the user's skin using infrared light. For example, the infrared light can pass through an aperture in the baseplate 202. In another example, one or more temperature sensors can be incorporated into the band 106 and can measure the temperature of the user's skin. For example, one or more temperature sensors can be woven into a fabric version of the band 106.

Figure 3:
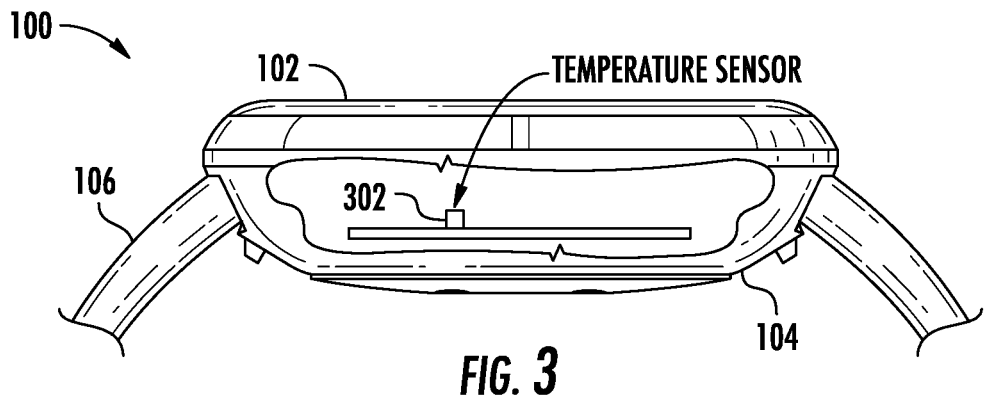
FIG. 3 depicts a side internal view of an example wearable device showing an internal device temperature sensor contained within a housing according to example embodiments of the present disclosure.

FIG. 3 depicts a side internal view of an example wearable device 100 showing internal device temperature sensor 302 contained within a device housing 104 according to example embodiments of the present disclosure. The internal device temperature sensor 302 can be configured to measure, and produce data relating to, a temperature of an internal space of the device housing 104 (e.g., an internal device temperature). The internal device temperature sensor 302 can also be comprised of multiple internal device temperature sensors. The internal device temperature sensor 302 may be contained within the device housing 104 of the wearable device 100, but is typically not in thermal contact with the user's skin. In one example, the internal device temperature sensor 302 can be affixed to an interior side of the device housing 104 (e.g., other than the baseplate 202). In another example, the internal device temperature sensor 302 can be affixed to a printed circuit board (e.g., the "motherboard") of the device 100.

Figure 4:
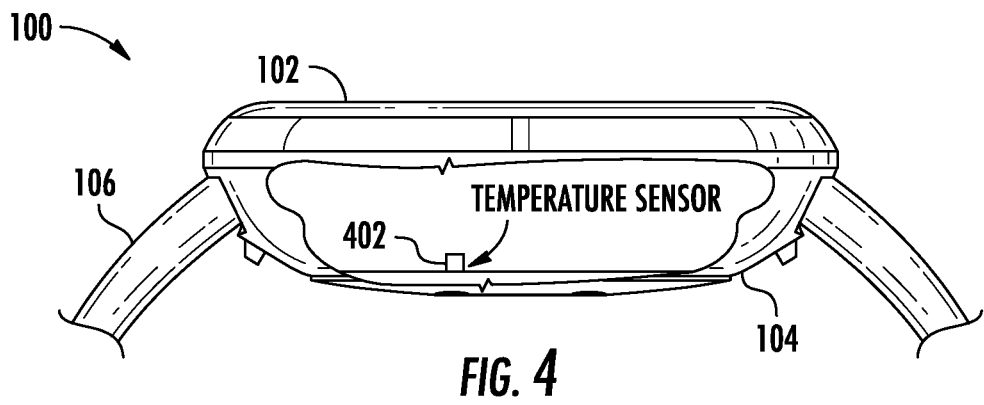
FIG. 4 depicts a side internal view of an example wearable device showing a skin temperature sensor contained within a housing according to example embodiments of the present disclosure.

FIG. 4 depicts a side internal view of an example wearable device 100 showing skin temperature sensor 402 contained within a device housing 104 according to example embodiments of the present disclosure. In some implementations, the skin temperature sensor 402 can be configured to be in physical contact with the user. In this way, the skin temperature sensor 402 can measure, and produce data relating to, a skin temperature of the user. In other implementations, the wearable device 100 can include a thermally conductive baseplate 202 configured to be in thermal contact with both the skin temperature sensor 402 and the user's skin. In such an embodiment, the skin temperature sensor 402 can be configured to measure, and produce data relating to, a temperature of the baseplate 202 that is also representative of a temperature of the user's skin. In yet further implementations, an infrared sensor can be included in the device 100 (e.g., within the housing 104) and can measure the temperature of the user's skin using infrared light. For example, the infrared light can pass through an aperture in the baseplate 202. The skin temperature sensor 402 can also be comprised of multiple skin temperature sensors (e.g., multiple different sensors taking multiple different approaches as described herein). Other arrangements are possible as well.

Figure 5:
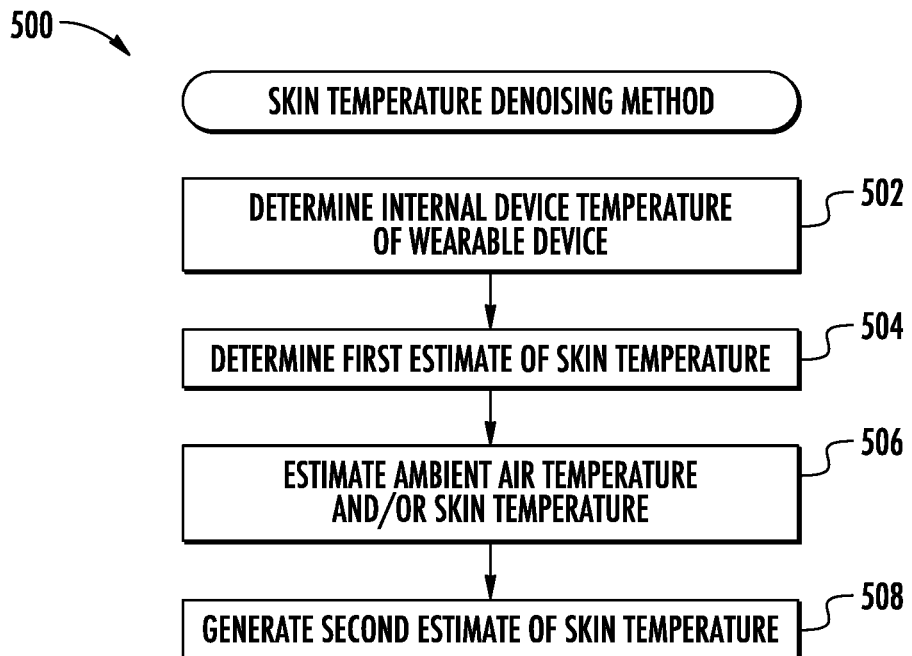
FIG. 5 depicts a flow of steps of an example skin temperature denoising method according to example embodiments of the present disclosure.

FIG. 5 depicts a flow of steps of an example skin temperature denoising method 500 according to example embodiments of the present disclosure. At step 502, the skin temperature denoising method 500 may determine an internal device temperature of a wearable device 100 worn by a user. The determination of the internal temperature of the wearable device 100 at step 502 can be based at least in part on sensor data from one or more internal device temperature sensors 302 contained on or within the wearable device 100. In another example, the determination of the internal temperature of the wearable device 100 at step 502 can be based at least in part on data from temperature sensors contained within other components of the device 100, such as temperature sensors existing within accelerometers and charging circuitry that produce temperature data as part of monitoring and calibrating their own output. At a next step 504, the skin temperature denoising method 500 may determine a first estimate of a skin temperature of a user. The determination of the first estimate of the skin temperature of the user at step 504 can be based at least in part on sensor data received from one or more skin temperature sensors 402 in physical and/or thermal contact with the user and contained within the wearable device 100. In another example, the determination of the first estimate of the skin temperature of the user at step 504 can be based at least in part on sensor data from one or more skin temperature sensors 402 in thermal contact with a baseplate 202. In this example, the baseplate 202 can also be configured to be in thermal contact with the user's skin when the wearable device 100 is worn by the user.

At step 506, the skin temperature denoising method 500 may estimate an ambient air temperature based at least in part on the first estimate of the skin temperature from step 504 and the internal device temperature of the wearable device 100 from step 502. The estimate of the ambient air temperature at step 506 can be based on a determination of the difference between the first estimate of skin temperature from step 504 and the internal device temperature of the wearable device 100 from step 502. In another example, the estimate of the ambient air temperature at step 506 may be the product of one or more smoothing or curve fitting processes of data sets corresponding to temperature differentials between the first estimate of skin temperature from step 504 and the internal device temperature of the wearable device 100 at step 502.

At step 506, the skin temperature denoising method 500 can also produce an intermediate estimate of skin temperature based at least in part on the first estimate of skin temperature from step 504 and the internal device temperature of the wearable device 100 from step 502. This intermediate estimate of skin temperature from step 506 can be further refined based at least in part on the ambient temperature estimate to aid in generating a second estimate of skin temperature at step 508 of the skin temperature denoising method 500. The intermediate estimate of skin temperature at step 506 may be the product of one or more smoothing or curve fitting processes of data sets corresponding to temperature differentials between the first estimate of skin temperature from step 504 and the internal device temperature of the wearable device 100 at step 502.

In yet another example, the estimate of the ambient air temperature or the intermediate estimate of skin temperature at step 506 can be determined by processing the first estimate of skin temperature from step 504 and the internal temperature of the wearable device from step 502 with a machine-learned model. In such an implementation, the estimate of the ambient air temperature or the intermediate estimate of skin temperature at step 506 can be a prediction output of a machine-learned model. For example, the machine-learned model can have been trained using a supervised learning approach on a set of training data including pairs of input data and a ground truth label. For example, for each pair, the input data can include example skin temperature and internal device temperature readings while the ground truth label can include a ground truth ambient temperature. For example, the set of training data can be collected over time from situations in which the wearable device is operating in an environment with a known ambient temperature. In some implementations, the set of training data can be generated using sensors existing within a test chamber that enables control of various temperatures, including temperatures representative of a user's skin and an ambient environment. By training on such a training dataset, the machine-learned model can be configured to produce a predicted ambient temperature or intermediate estimate of skin temperature based on the skin temperature and the internal device temperature. The machine-learned model can be any form of model including various neural networks (e.g., feed-forward neural networks, recurrent neural networks, transformer networks, etc.), linear models, support vector machines, a clustering model, etc.

In another example, the estimate of the ambient air temperature at step 506 can be adjusted based at least in part on additional ambient sensor data taken from additional ambient sensors contained on or within the wearable device 100. In an example, the estimate of the ambient air temperature at step 506 can be adjusted based at least in part on sleep data input by the user and collected by the wearable device 100 and/or other ambient data as described herein.

At step 508, the skin temperature denoising method 500 generates a second estimate of the user's skin temperature by refining the first estimate of the skin temperature based at least in part on the estimated ambient air temperature or the intermediate estimate of skin temperature from step 506. The second estimate of the skin temperature generated at step 508 can be the product of one or more smoothing or curve fitting processes of data sets corresponding to the estimated ambient air temperature or the intermediate estimate of skin temperature. In another example, the one or more smoothing or curve fitting processes of data sets can account for minor repositionings of the user, such as occurs when the user puts on a blanket or takes off a blanket, and other similar behavioral factors (e.g., general motion of the user). In this example, the one or more smoothing or curve fitting processes can modify a signal of skin temperature data points so that the signal is less influenced by temperature peaks caused by these behavioral factors.

In another example, generating the second estimate of the user's skin temperature at step 508 can involve modifying a confidence value associated with the second estimate of the skin temperature or the estimated ambient air temperature. In such an example, the confidence value can increase as the temperature differential between the first estimate of skin temperature or the estimated ambient air temperature and the internal temperature of the wearable device 100 decreases. In this example, a smaller temperature differential between the first estimate of skin temperature or the estimated ambient air temperature and the internal temperature of the wearable device 100 can equate to greater trust in the second estimate of skin temperature.

In some implementations, at step 508, the second estimate of the skin temperature can be determined by processing the first estimate of skin temperature from step 504, the intermediate estimate of skin temperature from step 506, and the estimated ambient temperature from step 506 with a machine-learned model. In such an implementation, the second estimate of the skin temperature at step 508 can be a prediction output of a machine-learned model. For example, the machine-learned model can have been trained using a supervised learning approach on a set of training data including pairs of input data and a ground truth label. For example, for each pair, the input data can include example estimated skin temperature and ambient temperature readings while the ground truth label can include a ground truth skin temperature. For example, the set of training data can be collected over time from situations in which the wearable device is operating in conjunction with a more accurate skin temperature sensor. By training on such a training dataset, the machine-learned model can be configured to produce a refined skin temperature reading (e.g., which reflects physiological events only rather than environmental events). In some implementations, the set of training data can be generated using sensors existing within a test chamber that enables control of various temperatures, including temperatures representative of a user's skin and an ambient environment. The machine-learned model can be any form of model including various neural networks (e.g., feed-forward neural networks, recurrent neural networks, transformer networks, etc.), linear models, support vector machines, a clustering model, etc.

Figure 6:
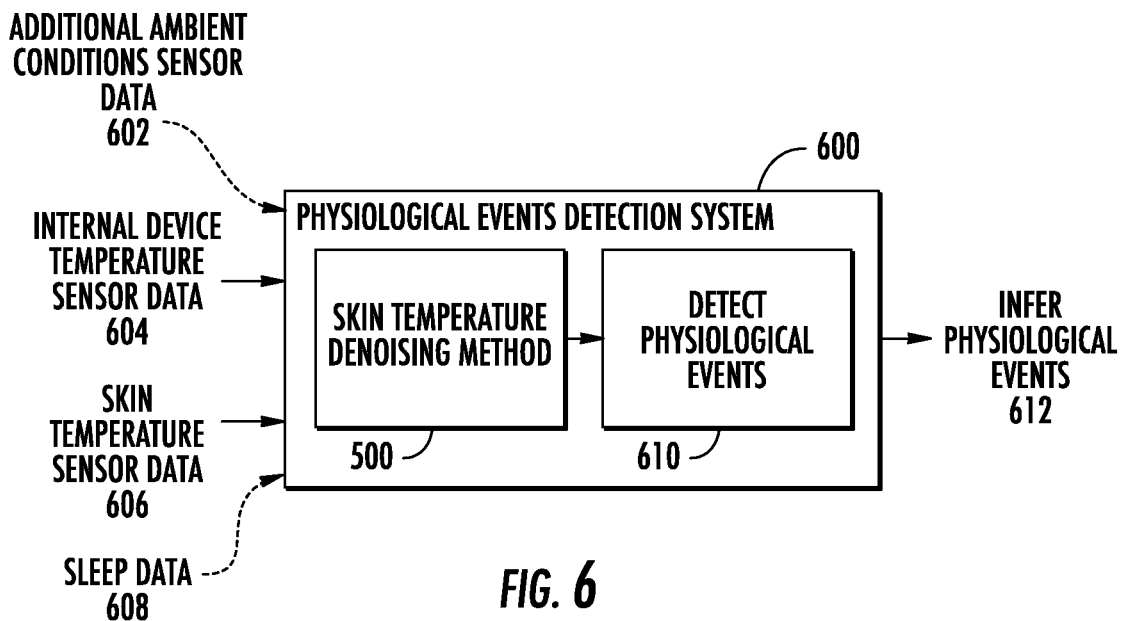
FIG. 6 depicts an example physiological events detection system according to example embodiments of the present disclosure.

FIG. 6 depicts an example physiological events detection system 600 according to example embodiments of the present disclosure. In an example, the physiological events detection system 600 can receive input in the form of additional ambient conditions sensor data 602, internal device temperature sensor data 604, skin temperature sensor data 606, and sleep data 608.

The additional ambient conditions sensor data 602 is optional and can include data from location sensors (e.g., global positioning sensors), geo-sensors, weather sensors, motion sensors, altitude sensors, altimeter temperature sensors, ambient light sensors, heart rate sensors, and other physiological sensors (e.g., blood oxygen sensors) contained on or within the wearable device 100. For example, by determining the location of the user via the location sensors, information from various databases about local ambient conditions (e.g., temperature or other weather data) can be obtained and used to guide the process. Likewise, data about heart rate and other physiological sensors can help understand changes in temperature which are physiological rather than environmentally driven.

The internal device temperature sensor data 604 can include data from one more internal device temperature sensors 302 contained on or within the wearable device 100. The skin temperature sensor data 606 can include data from one or more skin temperature sensors 402 contained on or within the wearable device 100 and in thermal contact with either the user or the baseplate 202 of the wearable device 100.

The sleep data 608 can include data collected by the wearable device 100 or input by the user. Examples of sleep data can include data to indicate whether the user is awake or asleep, a sleep coefficient of the user, and a heart rate of the user. In this example, if the user is asleep, the sleep data 608 can also include information to indicate whether the user is moving and a characterization of the type of sleep the user is experiencing (e.g., restless sleep, light sleep, deep sleep, REM sleep).

In this example of the physiological events detection system 600, the data inputs 602 and 608 can be processed in combination with the processing of data inputs 604 and 606 by performance of the skin temperature denoising method 500. As a component 610 of the physiological events detection system 600, physiological events of a user can be detected based at least in part on the data inputs 602 and 608 and the second estimate of skin temperature generated by performance of the denoising method 500. In such an example, the physiological events from component 610 can include a fever, a circadian rhythm, a menstruation cycle, ovulation, heat stress, and thermal comfort.

Detection of physiological events 610 can include detection or determination of a status of the physiological event such as an onset of the physiological event, and/or predictions about a future status of the event (e.g., peak fever expected to occur in next six hours). In another example, detection of physiological events 610 can involve smoothing a dataset of second estimates of skin temperature collected after an elevation in the user's skin temperature.

In component 612 of the physiological events detection system 600, the system can infer physiological events. Inferring physiological events at component 612 can involve the one or more processors contained within the device housing 104 to cause the display 102 to communicate to the user information concerning the physiological events detected from component 610.

Figure 7:
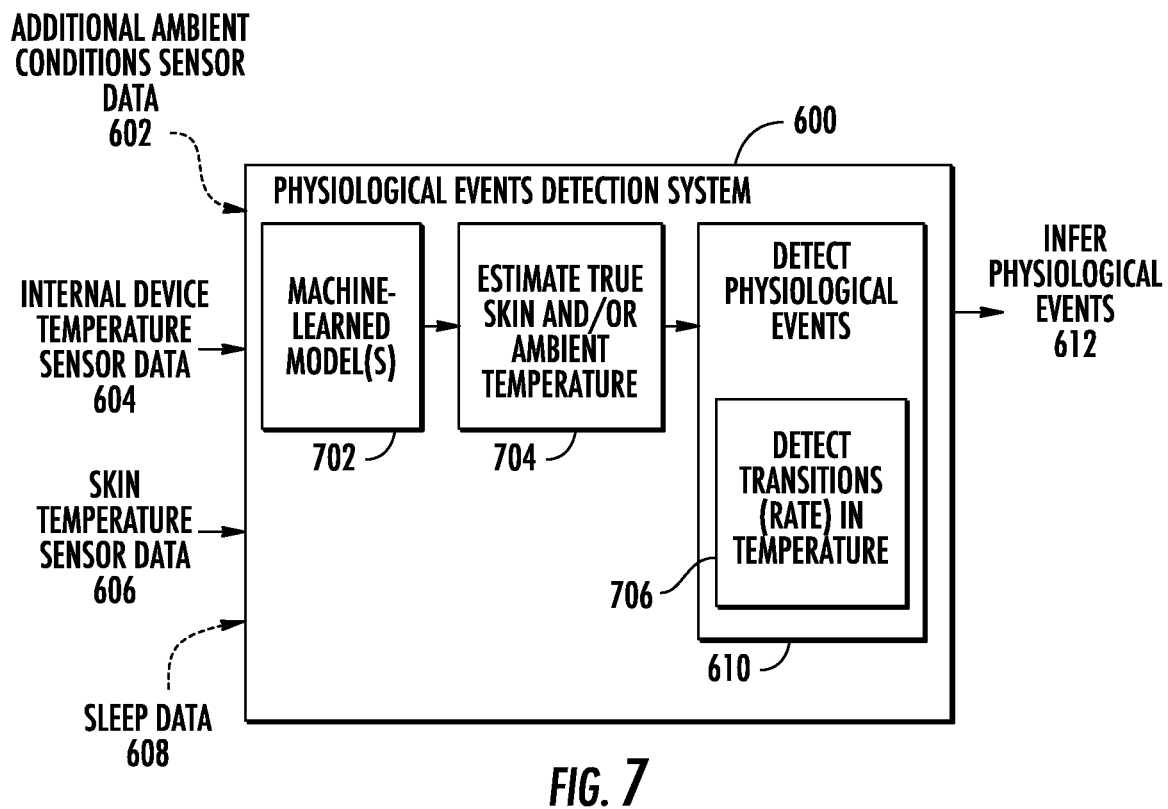
FIG. 7 depicts another example of a physiological events detection system according to example embodiments of the present disclosure.

FIG. 7 depicts another example of a physiological events detection system 600 according to example embodiments of the present disclosure. In this example, the physiological events detection system 600 can receive the same inputs 602, 604, 606, and 608 as received in the physiological events detection system from FIG. 6. The system of FIG. 7 can also detect and infer the same physiological events as described above for FIG. 6.

The physiological events detection system 600 of FIG. 7 can be configured to process the internal device temperature sensor data 604 and skin temperature sensor data 606 with a machine-learned model 702. In this example configuration, the machine-learned model 702 can include a linear regression model, a neural network (e.g., a recurrent neural network), or a clustering model. In such an example, the physiological events detection system 600 can receive an estimate of the ambient air temperature or an intermediate estimate of skin temperature as a prediction output by the machine-learned model 702. An estimate of the ambient air temperature or the intermediate estimate of skin temperature received in this way can also be used to estimate a true skin temperature of a user wearing the wearable device 100. In component 706, the physiological events detection system 600 of FIG. 7 can also be configured to detect and monitor transitions (e.g., rate of change) in estimates of the ambient air temperature and true skin temperature of the user. In this configuration, the detection of transitions in temperatures at 706 can contribute to the detection of physiological events at component 610 and the inference of physiological events at 612.

Figure 8:
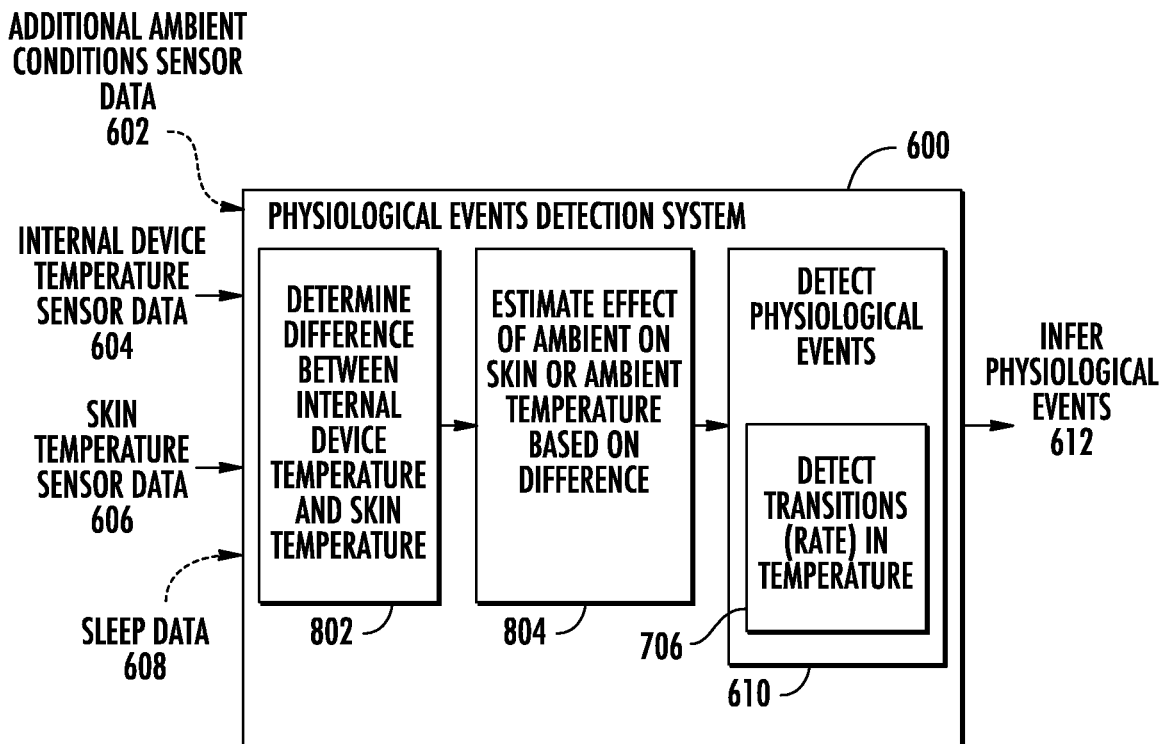
FIG. 8 depicts another example of a physiological events detection system according to example embodiments of the present disclosure.

FIG. 8 depicts another example of a physiological events detection system 600 according to example embodiments of the present disclosure. In this example, the system 600 can receive the same inputs 602, 604, 606, and 608 as received in the physiological events detection system from FIGS. 6 and 7. The system of FIG. 8 can also detect and infer the same physiological events as described above for FIGS. 6 and 7, including inputs relating to the detection of transitions in temperatures from component 706.

The physiological events detection system 600 from FIG. 8 can be configured with component 802 to determine a difference between the internal temperature of a wearable device 100 and a first estimate of skin temperature of a user wearing the wearable device 100. In component 804 of the physiological events detection system 600, the system can estimate an ambient air temperature or an intermediate estimate of skin temperature based on this difference. The estimated ambient air temperature or intermediate estimate of skin temperature from 804 can also be used to estimate the effect of the ambient air temperature on the skin temperature of the user by generating a second estimate of a user's skin temperature. The physiological events detection system 600 can also be configured to modify a confidence value associated with the second estimate of skin temperature or the estimated ambient air temperature from 804. In this configuration of the physiological events detection system 600, the confidence value can increase as the temperature differential between the first estimate of skin temperature or the estimated ambient air temperature and the internal temperature of the wearable device decreases. A smaller temperature differential determined at 802 can also mean it is less likely the estimated ambient air temperature is affecting the second estimate of skin temperature. The second estimate of skin temperature at 802 can also be used to estimate a core temperature of the user. In such a configuration, the physiological events detection system 600 can distinguish core temperature changes that are physiologically induced from core temperature changes that are environmentally induced.

Figure 9:
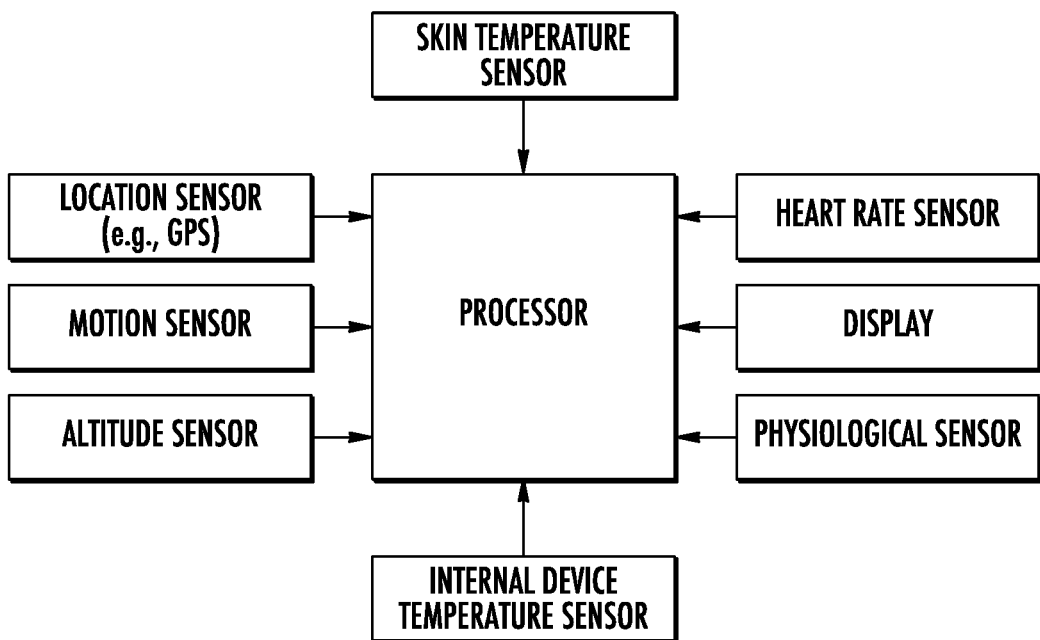
FIG. 9 depicts an example computing system according to example embodiments of the present disclosure.

FIG. 9 depicts an example computing system according to example embodiments of the present disclosure. The computing system can include a user computing device (e.g., a wearable device 100), which is shown in FIG. 9. The user computing device can in some implementations connect to a server computing system over a network. The server and network are not shown in FIG. 9.

The user device as shown in FIG. 9 can include one or more processors and a memory. The one or more processors can be any suitable processing device (e.g., a processor core, a microprocessor, an ASIC, a FPGA, a controller, a microcontroller, etc.) and can be one processor or a plurality of processors that are operatively connected. The memory can include one or more non-transitory computer-readable storage mediums, such as RAM, ROM, EEPROM, EPROM, flash memory devices, magnetic disks, etc., and combinations thereof. The memory can store data and instructions which are executed by the processor to cause the computing system of FIG. 9 to perform operations. Example operations can include the flow of steps of the skin temperature denoising method 500 and execution of component tasks described in the various configurations of the physiological events detection system from FIGS. 6, 7, and 8.

The user device of FIG. 9 can also include one or more user input components that receive user input. For example, the user input component can be a touch-sensitive component (e.g., the display 102 of the wearable device 100) that is sensitive to the touch of a user input object (e.g., a finger or a stylus). The touch-sensitive component can serve to implement a virtual keyboard. Example user inputs received by the computing system of FIG. 9 can include information about symptoms, sleep conditions, ovulation, menstruation, and other physiological information related to the user's health.

The user device of FIG. 9 can also include one or more sensors, including one or more skin temperature sensors 402 and one or more internal device temperature sensors 302. The skin temperature sensors 402 and internal device temperature sensors 302 can include negative temperature coefficient (NTC) thermistors, resistance temperature detectors (RTDs), thermocouples, and semiconductor-based sensors. Additional sensors of the computing system of FIG. 9 can be location sensors (e.g., GPS), motion sensors, altitude sensors, heart rate sensors, and other physiological sensors (e.g., blood oxygen level sensors). The location sensors may be cellular- or satellite-based GPS sensors. Example motion sensors include passive infrared (PIR), microwave, and dual tech/hybrid motion sensors. Example altitude sensors include pressure altimeters (e.g., aneroid barometers) and radio altimeters. Example heart rate sensors include optical transmission type pulse sensors (e.g., photoplethysmography (PPG)) and electrocardiography (ECD) sensors.

The server computing system (not shown in FIG. 9) can include one or more processors and a memory. The one or more processors can be any suitable processing device (e.g., a processor core, a microprocessor, an ASIC, a FPGA, a controller, a microcontroller, etc.) and can be one processor or a plurality of processors that are operatively connected. The memory can include one or more non-transitory computer-readable storage mediums, such as RAM, ROM, EEPROM, EPROM, flash memory devices, magnetic disks, etc., and combinations thereof. The memory can store data and instructions that are executed by the processor to cause the server computing system to perform operations.

In some implementations, the server computing system includes or is otherwise implemented by one or more server computing devices. In instances in which the server computing system includes plural server computing devices, such server computing devices can operate according to sequential computing architectures, parallel computing architectures, or some combination thereof.

The network can be any type of communications network, such as a local area network (e.g., intranet), wide area network (e.g., Internet), or some combination thereof and can include any number of wired or wireless links. In general, communication over the network can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

In some implementations, the user device of FIG. 9 can store or include one or more machine-learned models. For example, the machine-learned models can be or can otherwise include various machine-learned models such as various neural networks (e.g., feed-forward neural networks, recurrent neural networks, transformer networks, etc.), linear models, support vector machines, a clustering model, etc.

In some implementations, the one or more machine-learned models can be received from the server computing system over network, stored in the user device memory, and then used or otherwise implemented by the one or more processors. In some implementations, the user computing device can implement multiple parallel instances of a single machine-learned model.

Additionally or alternatively, the one or more machine-learned models can be included in or otherwise stored and implemented by the server computing system that communicates with the user device of FIG. 9 according to a client-server relationship. For example, the machine-learned models can be implemented by the server computing system as a portion of a web service (e.g., a data augmentation service). Thus, one or more models can be stored and implemented at the user device of FIG. 9 and/or one or more models can be stored and implemented at the server computing system. Additionally, some or all operations can be carried out at one location or multiple locations.

Example Data

Figure 10:
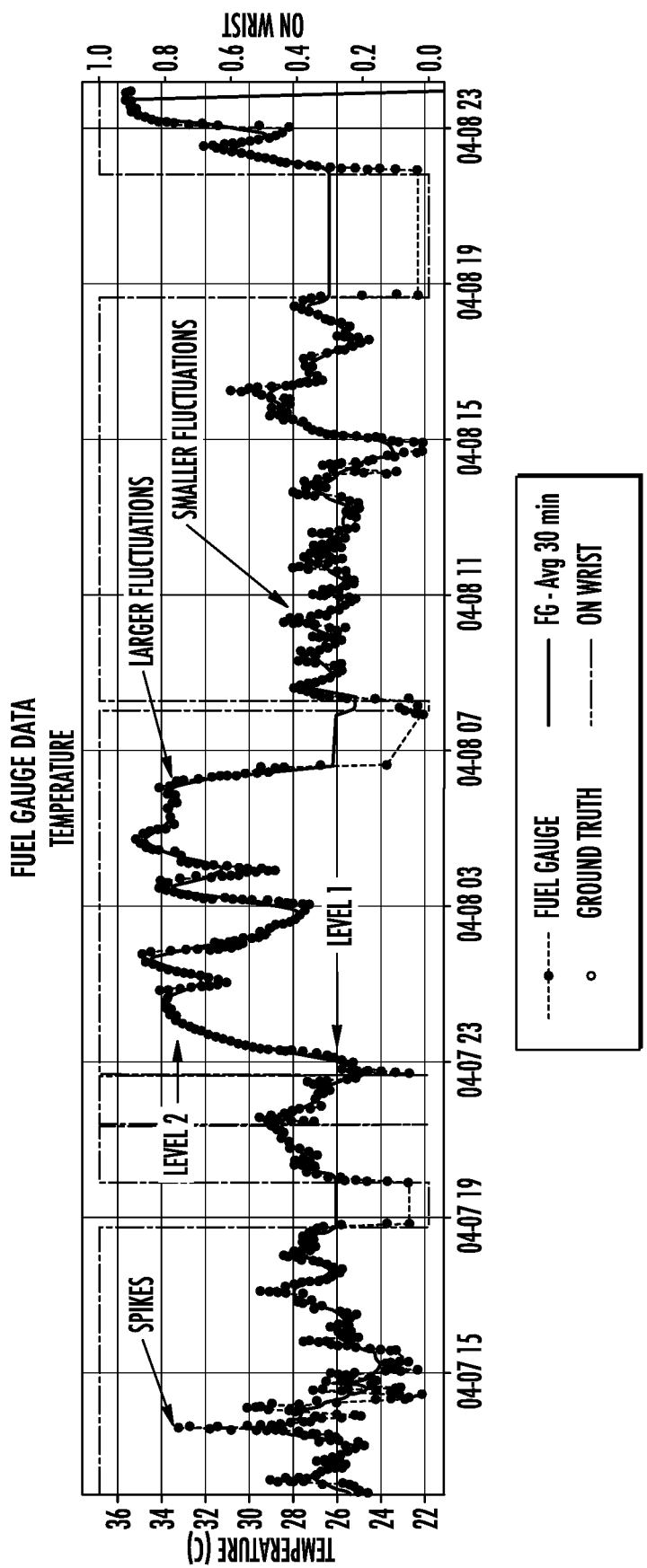
FIG. 10 depicts a graph of example temperature data of a wearable device according to example embodiments of the present disclosure.

FIG. 10 depicts a graph of example temperature data of a wearable device 100 according to example embodiments of the present disclosure. In FIG. 10, temperature measurements of the wearable device 100 are depicted at various times and at different states of usage by a user of the wearable device 100. FIG. 10 also includes a characterization of the magnitude of any fluctuations of temperature data and how those fluctuations compare to the time of day and whether or not the user is wearing the wearable device 100.

Figure 11:
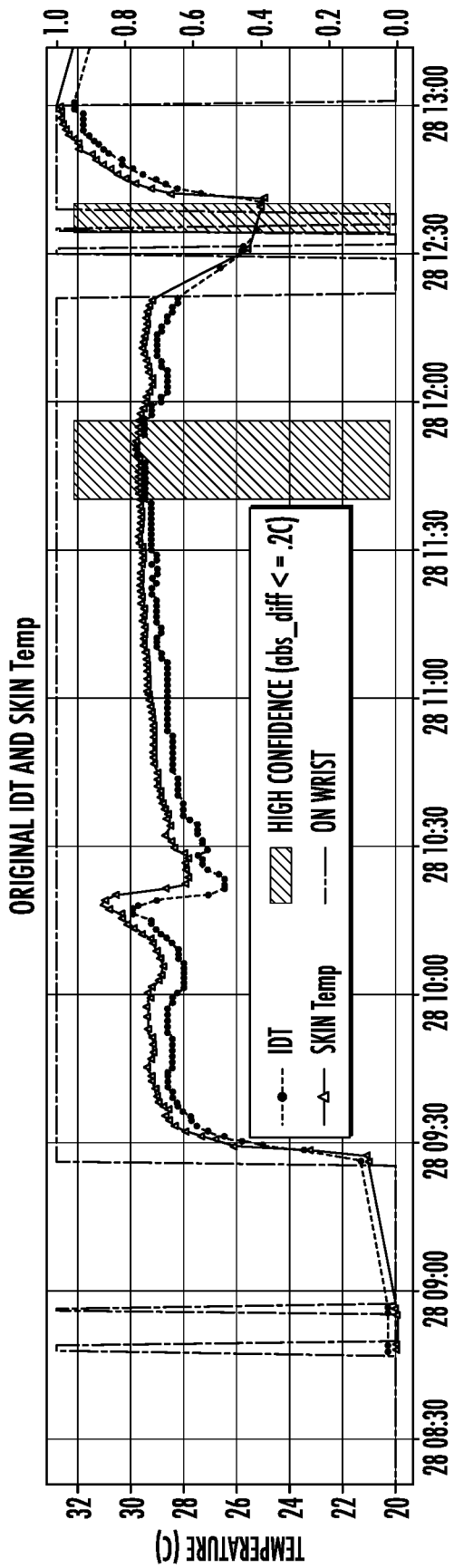
FIG. 11 depicts a graph of example internal device and skin temperature sensor data of a wearable device according to example embodiments of the present disclosure.

FIG. 11 depicts an example graph of temperature data from internal device temperature sensors 302 and skin temperature sensors 402 according to example embodiments of the present disclosure. In FIG. 11, temperature measurements of the internal device temperature sensor 302 and the skin temperature sensor 402 are depicted at various times and at different states of usage by a user of the wearable device 100. FIG. 11 represents recordings of temperature data from both sensors 302 and 402 based on the time of day and whether or not a user is wearing the wearable device. FIG. 11 further depicts time periods when the temperature differential between the measurements of the internal device temperature sensor 302 and skin temperature sensor 402 are largest and smallest. Time periods when the temperature differential between the two temperature sensors 302 and 402 is smallest (e.g., when the differential value is below a threshold value) are identified and shaded in FIG. 11. The time periods when the temperature differential is smallest also correlate with a higher confidence value in the estimate of a user's skin temperature, meaning it is less likely ambient temperature is causing changes in the skin temperature of the user of the wearable device 100.

Figure 12:
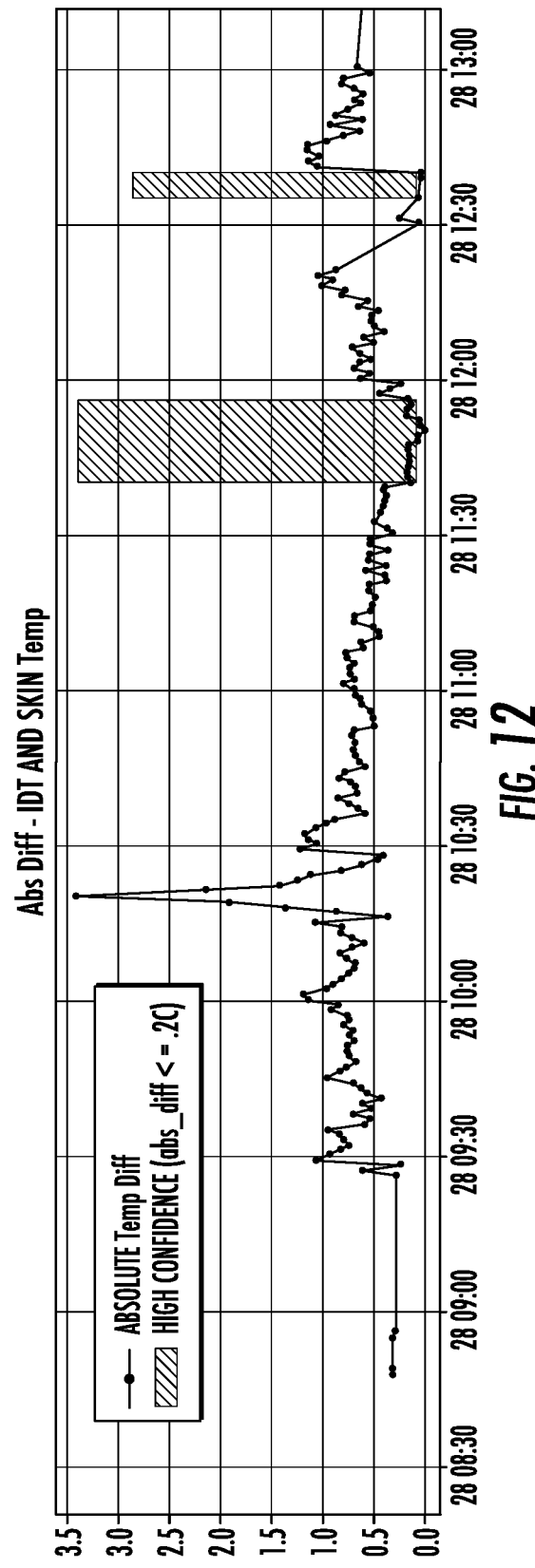
FIG. 12 depicts a graph of example internal device and skin temperature differential data according to example embodiments of the present disclosure.

FIG. 12 depicts an example graph of differential temperature data from internal device temperature sensors 302 and skin temperature sensors 402 according to example embodiments of the present disclosure. FIG. 12 is related to the graph depicted in FIG. 11, but instead plots a value of the temperature difference between the temperature measurements of the internal device temperature sensor 302 and the skin temperature sensor 402. FIG. 12 provides an alternate depiction (e.g., compared to FIG. 11) to illustrate time periods when the temperature differential value is largest and smallest. Time periods when the temperature differential value between the two temperature sensors 302 and 402 is smallest (e.g., when the temperature differential value is below a threshold value) are identified and shaded in FIG. 12. As in FIG. 11, time periods when the temperature differential is smallest also correlate with a higher confidence value in the estimate of a user's skin temperature, meaning it is less likely ambient temperature is causing changes in the skin temperature of the user of the wearable device 100.

Figure 13:
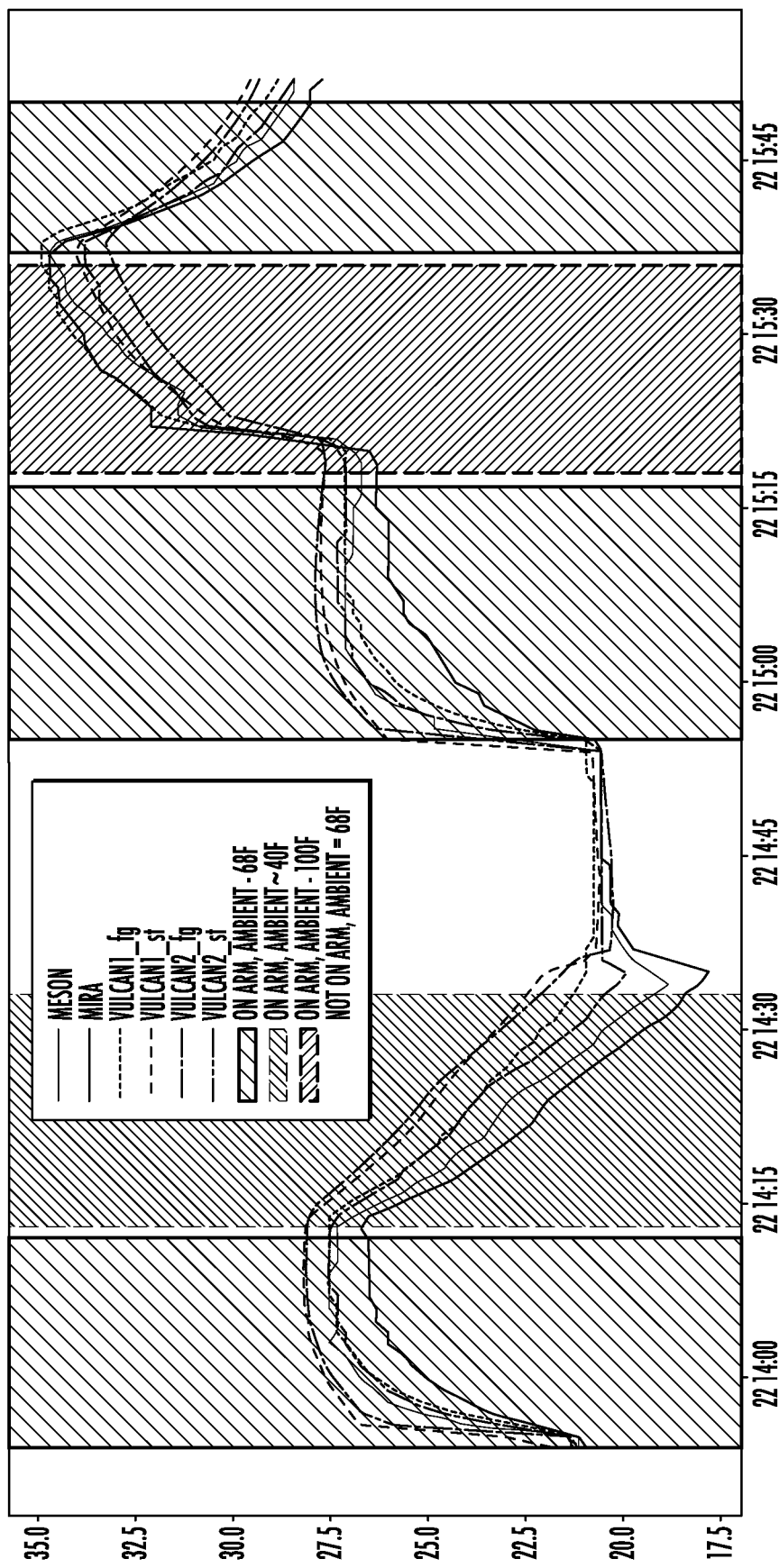
FIG. 13 depicts a graph of example temperature data of multiple wearable devices according to example embodiments of the present disclosure.

FIG. 13 depicts a graph of example temperature data of multiple wearable devices 100 according to example embodiments of the present disclosure. In particular, the graph of FIG. 13 plots temperature measurements of fuel gauge and skin temperature sensors 402 contained within the wearable devices 100 and how those measurements fluctuate when exposed to defined ambient temperature environments, for defined periods of time, and whether or not the wearable device 100 is on a wrist of a user.

Figure 14:
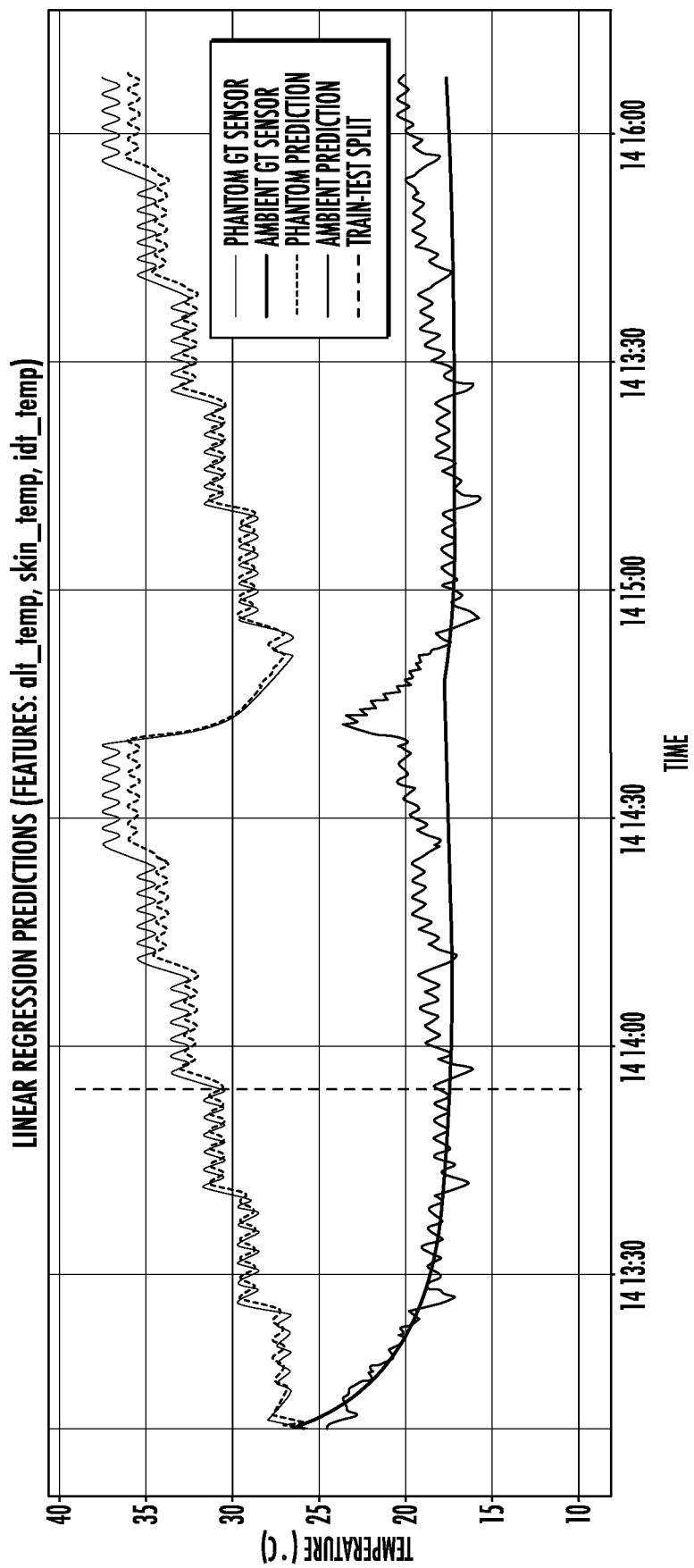
FIG. 14 depicts a graph illustrating an example linear regression model of ambient temperature estimate predictions according to example embodiments of the present disclosure.

FIG. 14 depicts a graph illustrating an example linear regression model of ambient temperature estimate predictions according to example embodiments of the present disclosure. In FIG. 14, ambient temperature estimate predictions are compared against temperature sensor data from sources including ambient and phantom ground truth sensors (further including altimeter temperature sensors, skin temperature sensors 402, and internal device temperature sensors 302) over a defined period of time.

Figure 15:
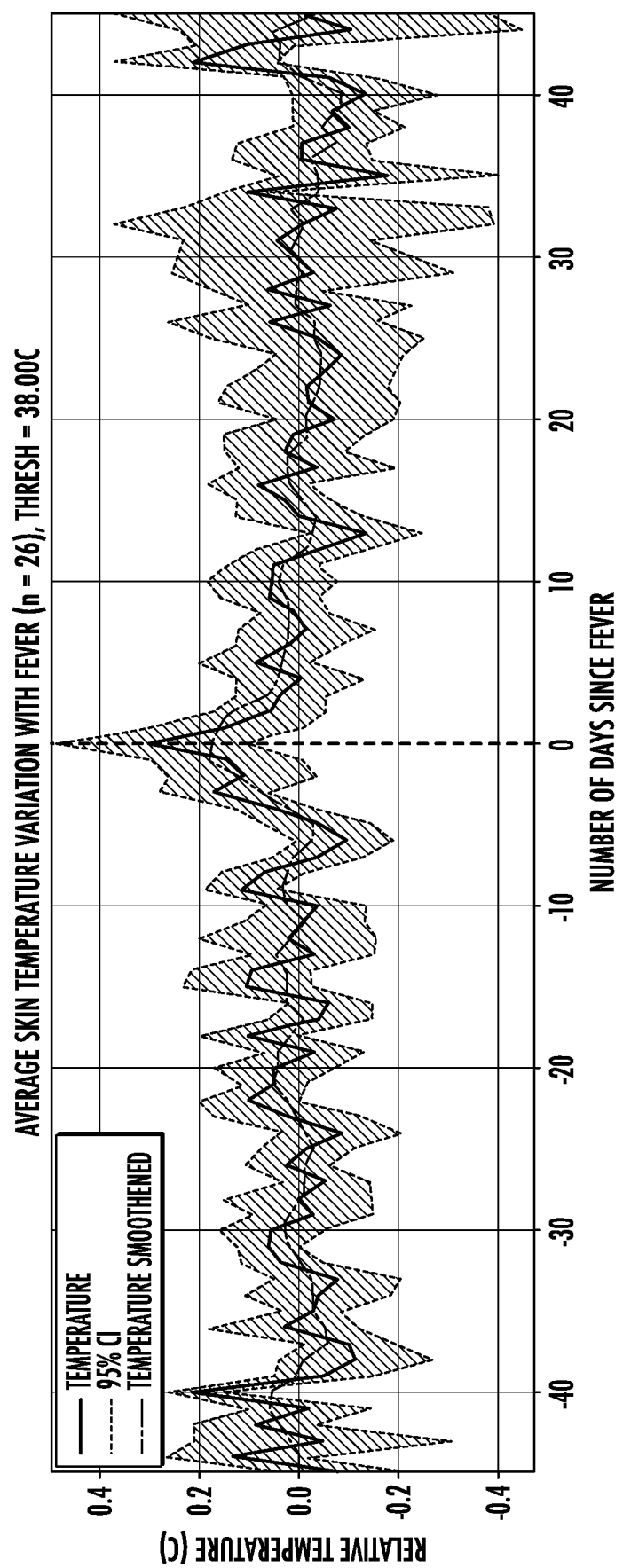
FIG. 15 depicts a graph of example skin temperature variations in relation to a number of days from a fever according to example embodiments of the present disclosure.

FIG. 15 depicts a graph of example skin temperature variations in relation to a number of days from a fever according to example embodiments of the present disclosure. In particular, FIG. 15 plots the variation of average skin temperature of a user, in terms of true and smoothened temperature data, in the days leading up to and following a fever.

Figure 16:
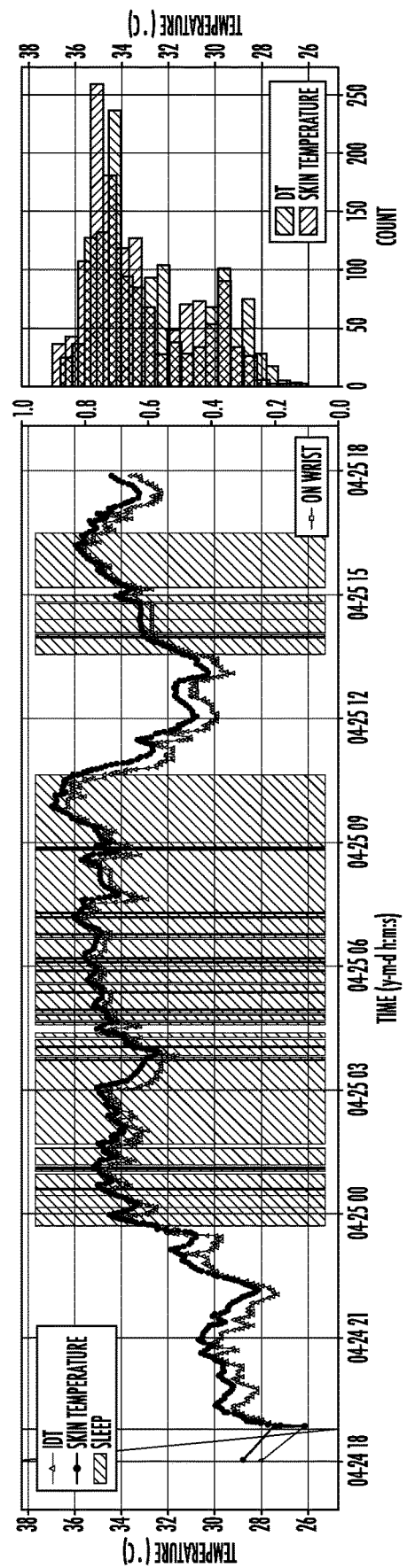
FIG. 16 depicts a graph of example temperature variations incorporating sleep data according to example embodiments of the present disclosure.

FIG. 16 depicts a graph of example temperature variations incorporating sleep data according to example embodiments of the present disclosure. More particularly, FIG. 16 represents recordings of temperature data from internal device temperature sensors 302 and skin temperature sensors 402 contained within a wearable device 100 taken over a defined period of time in which periods of sleep and a status of whether or not a user is wearing the wearable device 100 are identified and shaded. FIG. 16 also depicts a count value for internal device and skin temperature sensor measurements taken during the same period of time.

ADDITIONAL DISCLOSURE

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

In particular, although FIGS. 1 through 16 respectively depict steps performed in a particular order for purposes of illustration and discussion, the methods of the present disclosure are not limited to the particularly illustrated order or arrangement. The various steps of the skin temperature denoising method 500 and the physiological events detection system 600 can be omitted, rearranged, combined, and/or adapted in various ways without deviating from the scope of the present disclosure.

What is claimed is:

1. A computer-implemented method for providing skin temperature monitoring, the method comprising:
   determining, by a computing system comprising one or more computing devices, an internal device temperature of a wearable device worn by a user based on internal sensor data received from an internal device temperature sensor contained within the wearable device;
   determining, by the computing system, a first estimate of a skin temperature of the user based on skin sensor data received from a skin temperature sensor contained on or within the wearable device;
   estimating, by the computing system, an ambient air temperature based at least in part on the first estimate of the skin temperature and the internal device temperature, wherein estimating, by the computing system, the ambient air temperature based at least in part on the first estimate of the skin temperature and the internal device temperature comprises:
      adjusting, by the computing system, the ambient air temperature estimate based at least in part on sensor data from at least one of a location sensor, a geo-sensor, a weather sensor, a motion sensor, an altitude sensor, an altimeter temperature sensor, an ambient light sensor, or a heart rate sensor contained within the wearable device; and
   refining, by the computing system, the first estimate of the skin temperature based at least in part on the estimated ambient air temperature to generate a second estimate of the skin temperature.

2. The computer-implemented method of claim 1, further comprising determining, by the computing system, one or more physiological events based at least in part on the second estimate of the skin temperature.

3. The computer-implemented method of claim 2, wherein the one or more physiological events include at least one of an onset of fever, a circadian rhythm, menstruation cycle, ovulation, heat stress, or thermal comfort.

4. The computer-implemented method of claim 2, wherein determining, by the computing system, the one or more physiological events based at least in part on the second estimate of the skin temperature comprises:
  estimating, by the computing system, a core temperature of the user based at least in part on the second estimate of the skin temperature; and
  distinguishing, by the computing system, user core temperature changes that are physiologically induced from user core temperature changes that are environmentally induced.

5. The computer-implemented method of claim 2, wherein determining, by the computing system, the one or more physiological events based at least in part on the second estimate of the skin temperature comprises:
  monitoring, by the computing system, a rate of change in the second estimate of the skin temperature to detect a transition in the second estimate of the skin temperature; and
  determining, by the computing system, the one or more physiological events based at least in part on the detected transition in the second estimate of the skin temperature.

6. The computer-implemented method of claim 1, wherein estimating, by the computing system, the ambient air temperature based at least in part on the first estimate of the skin temperature and the internal device temperature comprises:
  determining, by the computing system, a difference between the first estimate of the skin temperature and the internal device temperature; and
  estimating, by the computing system, the ambient air temperature based at least in part on the difference between the first estimate of the skin temperature and the internal device temperature.

7. The computer-implemented method of claim 1, wherein estimating, by the computing system, the ambient air temperature based at least in part on the first estimate of the skin temperature and the internal device temperature comprises:
  processing the first estimate of the skin temperature and the internal device temperature with a machine-learned model; and
  receiving the ambient air temperature as a prediction output by the machine-learned model.

8. The computer-implemented method of claim 1, wherein estimating, by the computing system, the ambient air temperature based at least in part on the first estimate of the skin temperature and the internal device temperature comprises:
  adjusting, by the computing system, the ambient air temperature based at least in part on sleep data of the user collected by the wearable device.

9. The computer-implemented method of claim 1, wherein refining, by the computing system, the first estimate of the skin temperature based at least in part on the estimated ambient air temperature to generate the second estimate of the skin temperature, comprises modifying a confidence value associated with the second estimate of the skin temperature.

10. The computer-implemented method of claim 9, wherein modifying the confidence value associated with the second estimate of the skin temperature comprises increasing the confidence value as a temperature differential of the first estimate of the skin temperature and the internal device temperature decreases.

11. The computer-implemented method of claim 1, wherein:
  the internal device temperature sensor contained within the wearable device is comprised of multiple internal device temperature sensors; or
  the skin temperature sensor contained on or within the wearable device is comprised of multiple skin temperature sensors.

12. A wearable device, comprising:
  a device housing configured to be worn by a user;
  one or more processors included within the device housing;
  one or more skin temperature sensors included on or within the device housing and configured to produce skin temperature sensor data;
  one or more internal device temperature sensors included within the device housing and configured to produce internal device temperature sensor data; and
  non-transitory computer-readable memory included within the device housing and storing instructions that, when executed by the one or more processors, cause the wearable device to perform operations, the operations comprising:
    determining an internal device temperature within the device housing based at least in part on the internal device temperature sensor data received from the one or more internal device temperature sensors contained within the wearable device;
    determining a first estimate of a skin temperature of the user based on the skin temperature sensor data received from the one or more skin temperature sensors included on or within the device housing;
    estimating an ambient air temperature based at least in part on the first estimate of the skin temperature and the internal device temperature, wherein estimating the ambient air temperature based at least in part on the first estimate of the skin temperature and the internal device temperature comprises:
      adjusting the ambient air temperature estimate based at least in part on sensor data from at least one of a location sensor, a geo-sensor, a weather sensor, a motion sensor, an altitude sensor, an altimeter temperature sensor, an ambient light sensor, or a heart rate sensor contained within the wearable device; and
    refining the first estimate of the skin temperature based at least in part on the estimated ambient air temperature to generate a second estimate of the skin temperature.

13. The wearable device of claim 12, wherein the operations further comprise continuously observing a core temperature of the user, the core temperature of the user based at least in part on the second estimate of the skin temperature.

* * * * *